(12) United States Patent
Wippermann et al.

(10) Patent No.: US 10,254,288 B2
(45) Date of Patent: Apr. 9, 2019

(54) METHOD FOR SPECIES-INDEPENDENT MEASUREMENT OF COMPLEMENT ACTIVATION IN ANIMALS

(71) Applicant: Quidel Corporation, San Diego, CA (US)

(72) Inventors: Marieluise Wippermann, Seltisberg (CH); Janos Szebeni, Budapest (HU)

(73) Assignee: Quidel Corporation, San Diego, CA (US)

( * ) Notice: Subject to any disclaimer, the term of this patent is extended or adjusted under 35 U.S.C. 154(b) by 0 days.

(21) Appl. No.: 13/968,893

(22) Filed: Aug. 16, 2013

(65) Prior Publication Data

US 2015/0050671 A1  Feb. 19, 2015

(51) Int. Cl.
*G01N 33/68* (2006.01)

(52) U.S. Cl.
CPC ..... *G01N 33/68* (2013.01); *G01N 2333/4716* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,642,284 A * | 2/1987 | Cooper | | G01N 33/537 435/28 |
| 4,722,890 A | 2/1988 | Sanders et al. | | |
| 5,989,592 A * | 11/1999 | Collin | | A61K 31/737 424/520 |
| 2004/0170633 A1* | 9/2004 | Taylor et al. | | 424/155.1 |
| 2005/0222027 A1* | 10/2005 | Chiang et al. | | 514/12 |
| 2006/0115476 A1* | 6/2006 | Tedesco | | C07K 16/18 424/144.1 |
| 2007/0093443 A1* | 4/2007 | Madison et al. | | 514/44 |

FOREIGN PATENT DOCUMENTS

| | | |
|---|---|---|
| EP | 0128696 A1 | 12/1984 |
| WO | WO 2015/022566 A1 | 2/2015 |

OTHER PUBLICATIONS

Quidel, Microvue Complement SC5b-9 Plus, 6 pages, 2009, retrieved from http://www.quidel.com/sites/quidel.com/files/product/documents/a020_microvue_sc5b-9_plus_ruo.pdf on Dec. 30, 2014.*
Mahoney et al., Changes in the Haemolytic Activity of Serum Complement During Acute Babesia bovis Infection in Cattle. Z. Parasitenkd. 62, 39-45, 1980.*
Quidel, ELISA Immunoassays (EIA), 2 pages, retrieved from http://www.quidel.com/immunoassays/elisa-assay-enzyme-immunoassays, 2014, retrieved on Dec. 30, 2014.*
Quidel, An enzyme immunoassay to measure the total classical complement pathway activity in human serum, 12 pages, 2009, retrieved from http://www.quidel.com/sites/default/files/product/documents/a018_microvue_ch50_eq_english_10.pdf on Jul. 13, 2017.*
Measurement of Complement activation in non-primate sera by a hemolytic assay—CxH50, in Teco Medical Group, Clinical and Technical Review, 80 pages, 2010, retrieved from ftp://ftp.bmgrp.at/Austria/LifeScience/Complement_Biocompatibility.pdf on Jul. 13, 2017 (Teco).*
Quidel, retrieved from https://www.quidel.com/immunoassays/rapid-inflammatory-autoimmune-tests/microvue-ch50-eq-eia-kit on Jul. 13, 2017.*
Grant CK. Complement "specificity" and interchangeability: measurement of hemolytic complement levels and use of the complement-fixation test with sera from common domesticated animals Am J Vet Res. Oct. 1977;vol. 38 (No. 10):1611-7.
Barta O, Hubbert NL. Testing of hemolytic complement components in domestic animals. Am J Vet Res. Aug. 1978;vol. 39 (No. 8):1303-8.
Brown EJ, Ramsey J, Hammer CH, Frank MM. Surface modulation of classical pathway activation: C2 and C3 convertase formation and regulation on sheep, guinea pig, and human erythrocytes. J Immunol. 1983;131(1):403-8. Epub Jul. 1, 1983.
Xu H, Kitano E, Sato Y, Kobayashi C, Firdawes S, Kitamura H, et al. Studies of monkey complement: measurement of cynomolgus monkey CH50, ACH50, C4, C2 and C3. Xenotransplantation. 2008;15(1):14-9. Epub Mar. 13, 2008.
Ning J, Chang TM. Whole complement hemolytic activity (CH50) following infusion of stroma-free and polyhemoglobin solutions in rats. Biomaterials, artificial cells, and artificial organs. 1990;18(2):203-17. Epub Jan. 1, 1990. Abstract Only.
Robert A. Nelson Jr., Joerg Jensen, Irma Gigli, Noboru Tamura, Methods for the separation, purification and measurement of nine components of hemolytic complement in guinea-pig serum, Immunochemistry, vol. 3, Issue 2, Mar. 1966, pp. 111-135, ISSN 0019-2791, http://dx.doi.org/10.1016/0019-2791(66)90292-8. (http://www.sciencedirect.com/science/article/pii/0019279166902928).
T C Chanh, A A Benedict, and H Abplanalp, Association of Serum Hemolytic Complement Levels With the Major Histocompatibility Complex in Chickens, Jem, 144 (2): 555-561, 1976.
Moreno-Indias I, Dodds AW, Arguello A, Castro N, Sim RB: The complement system of the goat: haemolytic assays and isolation of major proteins. BMC Veterinary Research; 2012;8:91.
Clinical and Technical Review, "Complement Diagnostics: Haemocompatibility testing of medical devices, pharmaceuticals and blood products", TECOmedical AG, Retrieved from the internet: URL http://www.tecomedical.com/download_file?item_file_id=2378&item_file_code=01e9ed5eb4&file_key=0, pp. 1-76 (2013).

(Continued)

*Primary Examiner* — Andrea S Grossman
(74) *Attorney, Agent, or Firm* — McDermott Will & Emery LLP; Judy M. Mohr

(57) ABSTRACT

A method for species-independent measurement of complement (C) activation in animals. The method comprises taking samples in the range of 3-100 microliter of anticoagulated blood, plasma or serum of an animal (specimen), mixing the specimen with a specificity converting protein matrix (SCM), mixing to the specimen/SCM mixture an activator of the C system (Act), incubating the specimen/SCM/Act mixture at a temperature between 36° C. to 38° C. for a time of 5-120 min and determining the production of one or more human proteins by ELISA or other analytical methods.

15 Claims, 7 Drawing Sheets

(56) References Cited

OTHER PUBLICATIONS

Internation Search Report and Written Opinion from International Application No. PCT/IB2013/056680 dated Jan. 27, 2014, application now published as International Publication No. WO2015/022566, published on Feb. 19, 2015.

Qiu et al., "Complement activation associated with polysorbate 80 in beagle dogs", International Immunopharmacology, vol. 15, No. 1, pp. 144-149 (2013).

Weiszhar et al., "Complement activation by polyethoxylated pharmaceutical surfactants: Cremophor-EL, Tween-80 and Tween-20", European Journal of Pharmaceutical Sciences, vol. 45, No. 4, pp. 492-498 (2012).

* cited by examiner

Figure 1. Schematic illustration of the buildup of the classical pathway C3 convertase (A) and alternative pathway C3 convertase from animal and human C proteins during the PS-C3 method.

Figure 2. Complement activation by zymosan in various animal sera, supplemented with C3depl-NHS. Total activable C3 in different animals Fig. 3. Total activable porcine C3: Assay optimization: Effects of incubation time and serum proportion of C3depl-NHS

METHOD FOR SPECIES-INDEPENDENT MEASUREMENT OF COMPLEMENT ACTIVATION IN ANIMALS

FIELD OF INVENTION

In the field of immunology, the invention teaches a new method for species-independent measurement of the level of complement (C) in animals in vitro and in vivo, thereby extending the diagnostic and therapeutic arsenal of veterinarians, immunologists, physiologists and other scientists engaged in analyzing the C system. The invention also provides a tool for assessing the immune toxicity, and, hence, the safety of drugs, drug candidates, biomaterials and all molecules and agents that may exert adverse effects via C activation after exposure to blood or other C-containing body fluids. Yet further fields of the invention are enzymology, protein chemistry and evolution biology, inasmuch as our findings reveal a unique lack of specificity of the human C3 and C4 convertases, recognizing animal C3 and C4 from a variety of species.

BACKGROUND OF INVENTION

The Complement System and its Activation

The C system consists of some 30 plasma and cell membrane proteins. Along with three other proteolytic cascades in blood (coagulation, fibrinolytic and kinin-kallikrein systems), it plays an essential role in maintaining life. In particular, the C system provides the first line of defence against microbial or other pathogenic attacks, actively participating in and also orchestrating their clearance, and, at the same time, augmenting the body's specific immune response. Although the C system is best known for its role in immunity, the system also plays a key role in conception, tissue regeneration and in many more physiological functions (1-3).

It is well known in the art that 1) C activation can proceed via three pathways (classical, alternative and lectin), each involving different C proteins; 2) C activation leads to the liberation of anaphylatoxin (C3a, C5a) which then activate mast cells, basophils, platelets, and other inflammatory cells with resultant liberation of inflammatory mediators (histamine, PAF, prostaglandins, etc.); 3) the latter "secondary" mediators set in motion a complex cascade of respiratory, hemodynamic and hematological changes, helping the body's self-defence, but also causing adverse effects. Among these, certain drug-induced hypersensitivity reactions (HSRs) have been shown to be associated with C activation and were therefore called C activation-related pseudoallergy (CARPA) (4, 5). CARPA is particularly important for this invention, as we use animal models of CARPA to provide examples for the invention.

It is furthermore well known from the literature that the production of C4b and C3b can label cells for phagocytic uptake by macrophages, a process known as opsonisation, and that the membrane attack complex (MAC), which forms in the final steps of the activation cascade, can cause direct lysis of invader cells, as well as activation of inflammatory cells. Altogether, C activation is a complex, multifaceted immune phenomenon that has been the subject of clinical and basic research for many decades (6-44).

The C3 Convertases

This invention is based on the phylogenetic conservedness of C3 convertase and, hence, substitutability of human C3 by animal C3 without major loss of function. The C3 convertase is a multiprotein complexes that assembles upon C activation, and converts C3 to C3a and C3b (FIG. 1). Its structure and function have been studied in great detail since the early seventies (7-44). It has two types, called classical pathway (CP) and alternative pathway (AP) C3 convertases. Both can form on the surfaces of pathogens or particles that the immune system recognizes as foreign. The CP C3 convertase is formed from membrane-bound C4b after its binding of the protease C2a, while the AP C3 convertase is formed from membrane-bound C3b upon its binding of the protease Bb. These C3 convertases have the same activity, catalyzing the deposition and than covalent binding of a large numbers of C3b molecules on the activator surfaces, which enhances the visibility and uptake of the particles by macrophages, a phenomenon called opsonisation. One important role of the AP of C activation is the amplification of CP C3 convertase function to yield substantially more C3b molecules on the pathogen (45). Surface bound C3b nucleates the formation of CP and AP C5 convertases, which convert C5 to C5a and C5b. The former is the most potent anaphylatoxin, while the latter nucleates the membrane attack complex (MAC, C5b-9), which has cytolytic activity. Part of the formed C5b-9 binds to S protein to form SC5b-9, a soluble form of MAC, one of the possible end products of the PS-C3 method of this invention.

Existing Assays for Complement Activation in Man and Animals

There are a large number of different assays measuring C activation in human or animal blood, plasma or serum (3, 6, 46-90). Some of these assays are based on quantitation of protein split products arising upon the limited proteolysis during C activation by ELISA, RIA (rocket) or electrophoresis (91). To measure C activation in humans, commercial kits are available from a few companies, including Quidel's (San Diego, Calif.) MicroVue series kits measuring human C3a, C5a, C4d, Bb, SC5b-9 and CH50 (92-95). Membrane-bound C byproducts can be measured by Western blot or other immune histological analysis. Yet other assays of C activation measure the functional activity of the C cascade using hemolysis as endpoint. These hemolytic assays, also known as CH50 assays, usually utilize sheep or rabbit red blood cells (SRBC, RRBC), and quantitate the consumption of multiple activable (precursor) C proteins along the C cascade. In this reaction the rate-limiting factor is the C protein whose concentration is the lowest in the sample, which can significantly vary among different species and samples. Because the endpoint of haemolytic assays is a biological reaction (hemolysis), these assays are difficult to standardize (63, 70, 86, 88, 91, 93, 95-102). The spectrum of animals where haemolytic assays can be used has not been fully explored.

As for the measurement of C activation in animals, human ELISAs can be used for such purpose, in cases when the human antibodies used in the ELISA cross-react with the corresponding animal antigen. Examples include the measurement of baboon and old world (synomolgus) monkey C3a, Bb, C4d and SC5b-9 by the respective human ELISAs from Quidel. ELISA kits for animal C split products are also available from a few vendors, that measure rat C3, C3a, C5a, guinea pig C3a and C5a, dog SC5b-9, Bb, C4d and mouse C3a. It is also possible to estimate C activation in animals in vivo by measuring physiological or blood chemistry changes that are known to be due, or at least associated with C activation. These measurements include the recording of cardiovascular and hemodynamic changes (e.g., rise or fall of systemic and pulmonary arterial pressure, heart rate), ECG changes, blood levels of thromboxane A2, etc. (105-122).

The Invention

Figure 1:
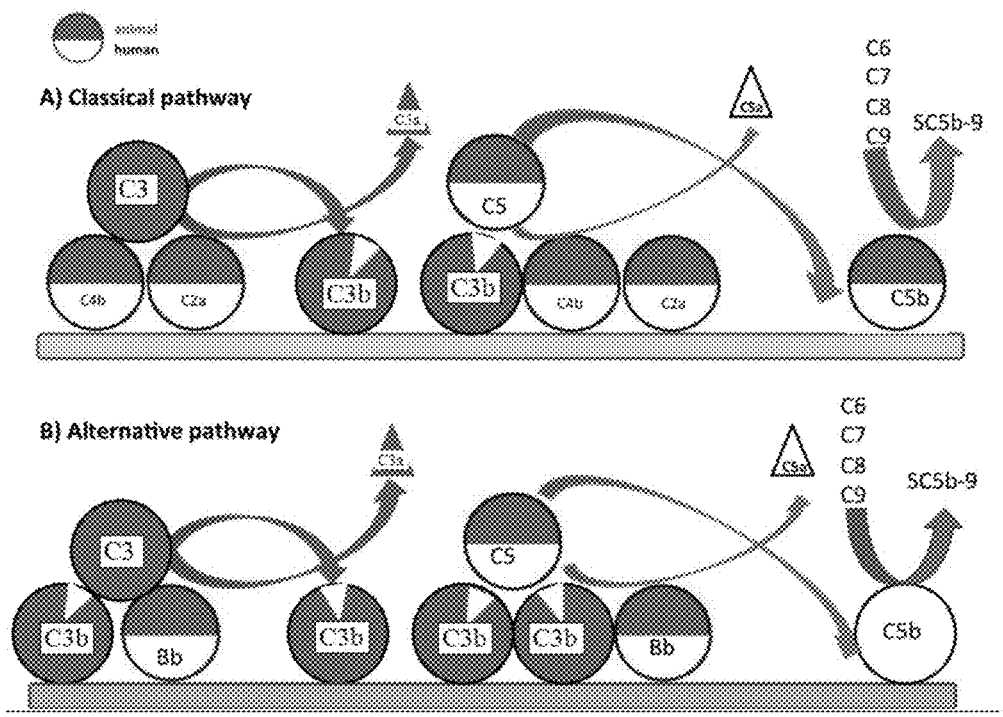
FIG. 1 shows a schematic illustration of the buildup of the classical pathway C3 convertase (A) and alternative C3 convertase from animal and human C proteins during the PS-C3 method.

The invention provides a common, universal assay for measuring C3 protein levels and consumption in animals by way of measuring the rise of human C split products using specific human ELISAs. Thus, human C split products serve as surrogate markers for animal C in blood, serum or plasma samples. In particular, the invention teaches the use of the human SC5b-9, CH50, C3a and C5a ELISA kits (such as marketed by Quidel Corporation, San Diego, Calif.) to measure the levels of C3 and C4 proteins in samples of different animals, whose level can be taken as measures of prior C activation. The invention utilizes a C3 specificity converting protein matrix or C4 specificity converting protein matrix for the determination of C3 and C4, respectively, which are mixed with the animal specimens, together with a known C activating substance, such as zymosan or HAGG. The mixture is incubated at a temperature between 36-38° C. for a sufficient period allowing development of human C3a, C5a and/or SC5b-9, which are measured with standard human ELISA or other human C5 and/or SC5b-9 measuring methods. The latter parameters indirectly quantitate the levels of C3 and/or C4 levels in the animal samples. Table 1 FIG. 1 shows the major steps involved in measuring animal C3 or C4 levels according to the invention.

The C3-SCM and C4-SCM allow the conversion of animal-specific C3 and C4 to be detectable and measurable by human-specific ELISAs. These matrices consist of C3 or C4-depleted normal human sera (C3depl-NHS, C4depl-NHS, marketed for example by Quidel Corporation, San Diego, Calif.), zymosan and/or HAGG or other C activator that trigger "intra-test activation", which show the total activable amount of C3 and C4 in the animal samples. It is important to distinguish "intra-test C activation" from "pre-test C activation", since the former is a necessary, unavoidable step in the assay, while "pre-test C activation" is a variable that may or may not be present, or may not be measurable by the PS-C3/C4 method of this invention. Also, because intra-test and pre-test C activation may utilize the same activator, e.g., zymosan or HAGG, it is easy to mix up or misinterpret the two processes.

The intra-test C activation involves incubation at preferably 37° C. of the test specimens of animal origin with C3-depleted (C3depl) or C4-depleted (C4depl) normal human serum (NHS) and measuring the production of human SC5b-9 (or C5a, or C3a) by ELISA following stimulation with zymosan or other C activator substance, such as HAGG. With animal C3 or C4 playing a rate-limiting role in the stimulated formation of human C activation by products, C3a, C5a or SC5b-9, the assay quantitates the level of animal C3 or C4. Because the actual levels of these proteins reflect previous C3 and/or C4 consumption, i.e., C activation, the assay enables quantitation of C activation in animal samples.

The test provides a quantitative measure of the level of active, i.e., activable C3 or C4 in the animal sample, taking the human SC5b-9 (or C3a, or C5a) as surrogate markers of animal C3 and C4. The total activable C3 or C4 in the sample is an ELISA OD in the 0-3.00 interval, obtained by subtracting the rise of C5a/SC5b-9 in the zymosan-free sample from that obtained in the zymosan-containing sample. The latter depends on the C status of animal samples, i.e., prior activation. Thus, the assay allows time-dependent quantitation of C activation in animal samples.

During intra-test C activation using animal-C3PM hybrid serum/plasma, the rate limiting step in the formation of human C5a or SC5b-9 is the activity of hybrid C3 convertase, consisting of animal C3 and animal and/or human C4b and C2a (classical pathway C3 convertase) or animal C3 and animal and/or human C3b and Bb (alternative pathway C3 convertase) (FIGS. 1A and B, respectively). The dark and white color circles in the figure illustrate the fact that the classical pathway hybrid C3 convertase builds up from animal C3 (dark) and animal (dark) and human (white) C4b and C2a, that are present in the complex in a ratio that corresponds to the volume ratio of animal to C3depl-NHS. Likewise, the alternative pathway C3 convertase builds up from animal C3 (dark) and animal (dark) and human Bb (white).

In C3depl-NHS, formation of human C5a or SC5b-9 will depend on the amount of animal C3 in the sample, which depends on prior C activation. Similar considerations apply to the C4depl-NHS assay, inasmuch as during the intra-test C activation using animal-C4 hybrid serum/plasma, the rate limiting step in the formation of human C5a or SC5b-9 is the activity of C1q2r2s, consisting of animal and/or human C1q, 2 animal and/or human C1r, and 2 animal and/or human C2s (C2 and C4 convertase). Consequently, in C4depl-NHS, formation of human C5a or SC5b-9 will depend on the amount of animal C4 in the sample, which depends on prior C activation via the classical pathway.

Novelty of the Invention

The invention addresses the problem that the methodical arsenal of measuring C activation in animals is much narrower than that available for humans. As mentioned above, there are commercially available ELISAs measuring C proteins in animals, these are offered only by a few vendors and are available for only a few proteins and few species. Most recently, a Chinese company was named as source of ELISA kits measuring SC5b-9 and Bb in beagle dogs (103), however, a follow-up paper questioned the reproducibility and validity of data (104). As an alternative approach, hemolytic assays have been used to measure C activation in different animals, but these assays are difficult to standardize (57), relatively insensitive and are considered irreproducible (87).

The present invention is based on the evolutionary conservedness of the C system, which fact is utilized in C research by the use of the SRBC to measure C consumption in animal serum specimens. In the latter, SRBC assay, it is the cytolitic function of the terminal C complex (MAC), formed from the animal C proteins, that is utilized for the measurement, namely, SRBC hemolysis. However, that hemolyis depends on the build-up of the TCC on the surface of SRBC, involving activation of the CP and the terminal chain. Hemolysis therefore will depend on the levels in the sample of all animal C proteins along the CP (C1-9), thus, the SRBC assay measures the composite activity of the CP in the animal serum sample. In contrast, because the assay mixture in the SC-C3 method in the present invention contains all human C proteins necessary for the detection of human SC5b-9 except C3, if the C3depl-NHS contains C5-9 is sufficient amounts, or in excess, the PS-C3 method measures ONLY the levels of animal C3 (or C4), i.e., it is possible to calibrate the system with known amounts of animal C3 (or C4) to make the method work like standard ELISAs equipped with standards for calibration. The present invention of specificity converter protein matrix allows therefore specific, pan-species measurement of animal C3 (or C4), which has not been possible to date with the SRBC or other assays.

Based on the above considerations, the present discovery that the animal C3 is used by the human C3 convertase to produce SC5b-9 that is recognized by Quidel's SC5b-9 kit as a human neoantigen, represents a serendipitous observation that could not be inferred directly from the existence and use of the SRBC assay to measure animal C. To our best knowledge, nor is there example in biology that a human enzyme complex would utilize as its functional part proteins from a variety of animals without major loss of activity. This "promiscuity" of the human C3 is not obvious in the C literature even for experts with substantial experience in the art.

Therefore, the present invention provides a method for species-independent measurement of complement (C) activation in animals comprising the steps of taking samples in the range of 3-100 microliter of anticoagulated blood, plasma or serum of an animal (specimen), mixing the specimen with a specificity converting protein matrix (SCM), mixing to the specimen/SCM mixture an activator of the C system (Act), incubating the specimen/SCM/Act mixture at a temperature between 36° C. to 38° C. for a time of 5-120 min and determining the production of one or more human proteins by ELISA or other analytical methods.

Claim 2 describes method according to claim 1, wherein in step a) the samples of blood, plasma or serum are taken from bovine, chicken, goat, guinea pig, horse, mouse, pig, rabbit, rat, sheep, turkey or dog.

Claim 3 describes a method according to claim 1 or 2, wherein in step b) the mixing of the specimen with a specificity converting protein matrix (SCM) is done at a low specimen/SCM ratio of 1-4:9-6.

Claim 4 describes a method according to claim 1, wherein SMC in step b) is either C3-depleted normal human serum (C3depl-NHS) or lyophilized C3depl-NHS (lyoC3depl-NHS) or C4-depleted normal human serum (C4depl-NHS) or lyophilized C4-depleted normal human serum (lyoC4depl-NHS).

Claim 5 describes a method according to claim 1, wherein SCM in step b) is supplemented with purified or recombinant human C5, preferably at a concentration that presents in the total test volume concentration of C5 in human blood.

Claim 6 describes a method according to claim 1, wherein SCM in step b) is supplemented with purified or recombinant human C5, C6, C7 and C9, preferably at individual concentrations which in the total test volume present their physiological concentration in human blood.

Claim 7 describes a method according to claim 1, wherein SCM in step b) is a mixture of purified or recombinant human C5, C6, C7 and C9, preferably at individual concentrations which in the total test volume correspond to their physiological concentration in human blood.

Claim 8 describes a method according to claim 1, wherein in step c) the activator of the C system (Act) is zymosan (in the 0.1-10 mg/mL range), or HAGG (in the 0.1-20 mg/mL range), or a liposomal drug like Ambisome (in the 0.01-100 mg phospholipid/mL range), or a surfactant like Cremophor EL or PS-80 (in the 0.01-100 mg/mL range).

Claim 9 describes a method according to claim 1, wherein in step d) the incubating of the specimen/SCM/Act mixture is done at 37° C. for 45-60 min with shaking.

Claim 10 describes a method according to claim 1, wherein in step e) human SC5b-9 ELISA is as endpoint for the quantification of C activation in different animal sera.

Claim 11 describes a method according to claim 1, wherein in step e) human C5a ELISA is used as endpoint for the quantification of C activation in different animal sera.

Claim 12 describes a method according to claim 1, wherein in step e) human C3a ELISA is used as endpoint for the quantification of C activation in different animal sera.

Claim 13 describes a method according to claim 1, wherein in step e) a human CH50 kit is as endpoint for the quantification of C activation in different animal sera, which kit detects human SC5b-9.

Claim 14 describes a tool for assessing the immune toxicity of drugs, drug candidates, biomaterials and all molecules and agents that may exert adverse effects via C activation after exposure to blood or other C-containing body fluids, which tool a) utilizes the steps specified in claim 1, b) utilizes animal specimens such as blood, plasma or serum, c) is applicable in all animals, d) utilizes a specificity converter protein matrix, such as specified in claims 4-7, e) utilizes ELISA kits specified in claims 10-13.

EXAMPLES

Example 1: Evidence that C3-Depl-NHS Enables Zymosan or HAGG to Cause C Activation in Animal Serum that can be Measured by Human SCSb-9 ELISA Goal To provide evidence that C3-depl-NHS enables zymosan or HAGG to cause C activation in animal serum that can be measured by human SC5b-9 ELISA.

Materials and Methods

Materials

PBS 5× concentrate. pH 7.1: 40.5 mM di-sodium hydrogen phosphate dihydrate (Roth, 4984), 7.5 mM potassium dihydrogen phosphate (Roth, 3940), 0.68 M sodium chloride (Roth, 3957), 13.5 mM potassium chloride (Sigma Aldrich, 31248).

Zymosan A from *Saccharomyces cerevisiae* was from Sigma Aldrich, 24250.

Heat aggregated gamma globulin (HAGG)~50 mg/ml, Quidel cat No: Al 14

C3-depleted NHS, Quidel cat No: A508

SC5b-9 kit, Quidel cat No: A009

Stop solution: 0.2 M EDTA disodium dihydrate (Roth, 8043)

Animal sera was obtained from Quidel/TECOmedical and/or other vendors/sources.

Methods

The sera that were not of commercial origin were prepared from freshly drawn blood, which was let to clot at room temperature for 10-30 min, followed by centrifugation and collection of the supernatant. The serum was then stored at −80° C. until use. Zymosan (final concentration: 1.3 mg/ml) was prepared by suspending it at 2% in 0.15 M sodium chloride, boiling in a water bath for one hour, then centrifuged for 30 minutes at 4000 rpm. The supernatant was discarded and the residue suspended evenly in 0.15 M sodium chloride to 2%.

HAGG was diluted 100-fold (to a final concentration: 0.5 mg/mL).

10 µL Zymosan (20 mg/ml) or HAGG were incubated for 1 h at 37° C. with a mixture of 20 µL animal serum, and 20 µl C3depl-NHS 100 µl PBS. The reaction was stopped by the addition of the 10 µl stop solution, and 100 µL of a 1:1600 dilution from the mixtures were applied to the wells of the SC5b-9 ELISA plates to measure the formation of SC5b-9 as specified by the manufacturer.

Results

Incubation of animal sera from 9 species with C3d-NHS and zymosan or HAGG led to rises of human SC5b-9 in the 120-2947% range. The effect of zymosan or HAGG decreased in the following order; goat>bovine>guinea pig>turkey>mouse>rabbit>horse>rat>chicken). These observations demonstrate that the use of C3d-NHS enabled the detection of C activation by zymosan and/or HAGG in all these animals using the human SC5b-9 ELISA kit.

Figure 2:
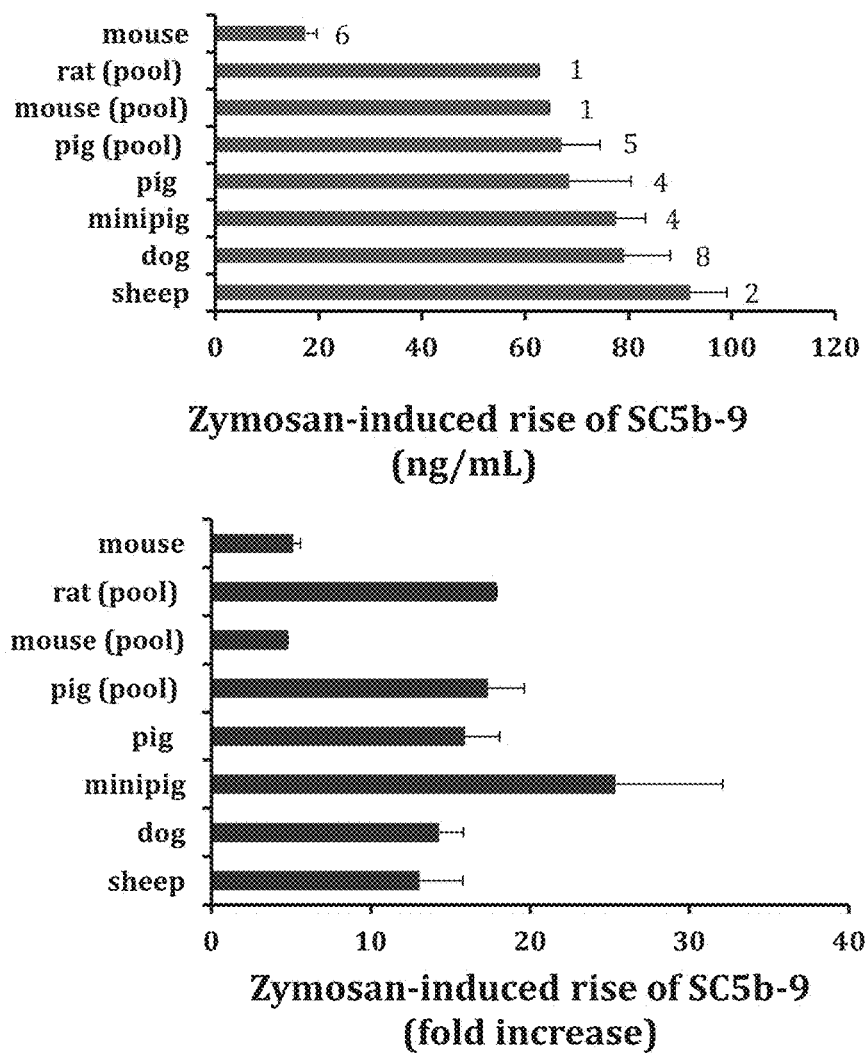
FIG. 2 shows complement activation by zymosan in various animal sera, supplemented with C3depl-NHS. Total activable C3 in different animals.

FIG. 2, shows similar experiments performed in multiple animals in each species, using only zymosan as intra-test C activator. Essentially the same results were obtained inasmuch as in all sera significant rises of SC5b-9 were observed, although in this series minipigs, rats and pigs showed the greatest rise of SC5b-9, expressed as a ratio (fold increase), while in absolute terms, i.e., rise of SC5b-9 in ng/mL, sheep and dogs were in the frontline.

Conclusions:
Measuring human SC5b-9 provides a common endpoint for the quantification of C activation in different animal sera.
Different animals exhibit different sensitivities to C activation by HAGG and zymosan.
The data provide proof of concept for the use of SC-C3 ELISA, as described in the example, for measuring C activation in animals in vitro.

Example 2: Essential Ingredients and Endpoints of the Pan-Species C3 Method

Goal

To show that the presence of C3-depl-NHS is a necessary precondition for using the PS-C3 method, and that both SC5b-9 and C5a can be endpoints.

Materials and Methods
Materials:
Same as in Example 1.
Rat sera was obtained as described in Example 1. The experiment presented in example 2 utilized pooled rat serum.

Results

The effects of C3depl-NHS on C activation by zymosan and HAGG in pooled rat serum[[,]] were measured by the human SC5b-9 and C5a ELISA kits. Significant activation was seen in sera exposed to zymosan and HAGG, only in the presence of the specificity converter C3d-NHS. Zymosan was superior activator than HAGG. C activation was measurable both by the SC5b-9 and C5a kits, with the SC5b-9 kit yielding higher values.

Conclusions:
Incubation of pooled rat serum with either zymosan or HAGG led to C activation only if the specificity converter C3d-NHS was present.
This activation was caused by the activators (zymosan or HAGG) but not by PBS.
C activation was measurable both by the SC5b-9 and C5a kits.
Zymosan is superior activator than HAGG.
SC5b-9 is more sensitive measure of C activation than C5a.

Pooled rat serum was incubated with either zymosan or HAGG, in the absence or presence of specificity converter C3d-NHS. C activation was measured by the human SC5b-9 or C5a kit. Entries are ng/mL obtained after 60 min incubation. Activation %, activated samples/PBS×100.

Example 3: Complementation of C3depl-NHS with Purified C Proteins: Effects on Activable C3 in Pig Serum Goal To explore whether complementation of C3depl-NHS with purified human C proteins would improve the sensitivity of pan-species C3 method in the case of pig serum.

Materials and Methods
Materials and Methods:
Same as in Example 1.
Purified C proteins C5, C6, C7, C8 and C9 were obtained from Quidel.

Results

The effects of the addition of C5, C6, C7, C8 and C9 on zymosan-induced SC5b-9 production in pooled pig serum includes:
the addition of human C5-C9, just as C5 alone, increased the maximal activable C3 level, and thus the dynamic rang of the pan-species C3 method, by about 5-fold,
the addition of C5 alone also yielded significant improvement in the activation/baseline ratio.

Conclusions:
Enriching of C3depl-NHS with human C5 significantly increases the assay's dynamic range, and, hence, sensitivity, in pig serum.

Example 4: Replacement of C3depl-NHS with Purified C Proteins

Goal

To explore whether the C3depl-NHS can be replaced by purified C proteins in the terminal chain.

Materials and Methods
Materials and Methods:
Same as in Example 1.
Purified C proteins C5, C6, C7, C8 and C9 were obtained from Quidel.

Results

The effects of replacing the C3depl-NHS with various combinations of C5, C6, C7, C8 and C9 on zymosan-induced SC5b-9 production in pooled pig serum includes:

It is possible to substitute C3depl-NHS with purified C proteins, with best results achieved with a physiological mixture of C5, C6, C7 and C9, C8 is not necessary for the activity of purified C matrix, and it may actually reduce the efficacy of the C5-7+C9 mixture.

Conclusions:

It is possible to substitute C3depl-NHS with purified C proteins

Example 5: Complement Activation by Different Activators in Dog Serum

Goal

To compare the C activating effect of zymosan in dog serum with other known C activators in dogs, using the pan-species C3 method.

Materials and Methods

Materials and Methods

Dog blood was obtained from WellPet Animal Clinic (Kecskemét, Géza Fejedelem körút 51. Hungary). Serum was prepared by letting the blood clot at 4° C. for about 10 min (dog blood clots rapidly), followed by centrifugation and collection of supernatant serum. The serum was then stored at −20° C. and then at −80° C. until use (within days).

Other materials and methods are the same as described for Example 1. The measurement of SC5b-9 was done using Quidel's SC5b-9 kit.

Results

Further experiments were performed, in which dog serum was used to compare C activation by zymosan, Cremophor EL and Tween 80, using the CH50 ELISA to determine SC5b-9. Zymosan and Tween 80 were equally effective activators, causing ~30-fold rise of SC5b-9, over PBS control, while Cremophor EL was still a potent activator, causing-10-fold rise in this analyte.

Conclusions:

The pan-species C3 method works in the case of dog serum, too.

The tested activators all showed significant activation of dog C.

Example 6: Complement Activation by Zymosan in Porcine Serum In Vitro

Goal

To compare the sensitivity of the pan-species C3 method in human and porcine sera in measuring zymosan-induced C activation, and role of C5a in the efficacy of C3depl-NHS.

Materials and Methods

Pig blood was obtained from male, castrated Yorkshire pigs weighing 12-25 kg. Serum was prepared by letting the blood clot at room temperature for ~30 min, followed by centrifugation and collection of supernatant serum. The serum was then stored at −80° C. until use (within days).

Other materials and methods are the same as described for Example 1. The measurement of SC5b-9 was done using Quidel's SC5b-9 kit.

Results

The sensitivity of the human SC5b-9 assay measuring zymosan-induced C activation in man and porcine serum was compared. The data show approximately identical sensitivity, inasmuch as the fold-rise over PBS background (5 and 6) was near identical. The data also shows that replacing the C3depl-NHS with recombinant human C5 only does not allow the measurement of C activation in pig serum.

Conclusions:

The pan-species C3 method shows equal sensitivity to measure C activation in human and porcine serum.

The use of C3depl-NHS is necessary for the assay to work for measuring C activation in porcine serum, it is not replaceable only by rhuC5.

Example 7: The Use of Lyophilized C3depl-NHS to Measure C Activation in Porcine Serum Goal To explore whether lyophilization has any impact on the use of the pan-species C3 method for the detection of C activation in porcine serum.

Materials and Methods

Similar studies as described in Example 3.

Results

The performance of the human SC5b-9 assay measuring zymosan-induced C activation in porcine blood, using C3depl-NHS as fluid, or as lyophilized powder, reconstituted with water soon before the experiment, was compared. The data suggest only minor (20-30%) decrease in assay sensitivity when lyophilized C3depl-NHs was used.

Conclusions:

It may be possible to use lyophilized C3depl-NHs for the pan-species C3 method as source of specificity converting protein matrix.

Example 8: Optimization of the Measurement of C Activation in Porcine Serum by the Pan-Species C3 Method Via Changing the Animal Serum-to-C3depl-NHS Ratio Goal To find out the optimal incubation time and ratio of C3depl-NHS to animal serum for measuring zymosan-induced C activation in porcine serum.

Materials and Methods

Figure 3:
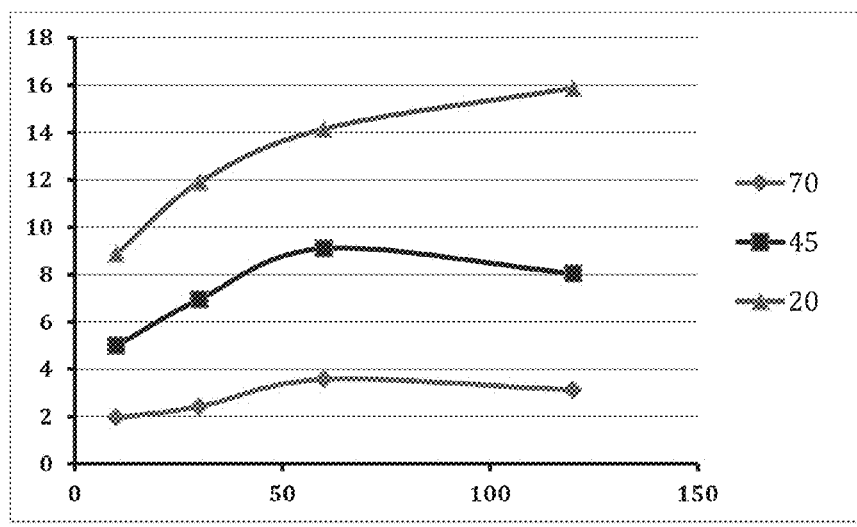
FIG. 3 shows total activable porcine C3: Assay optimization showing effects of incubation time and serum proportion of C3depl-NHS.

Similar studies as described in Example 3, except that the ratio of C3depl-NHS and animal serum was changed as specified in FIG. 3.

Results

FIG. 3 shows the time course of SC5b-9 rise in porcine serum, measured by the PS-C3 method, wherein the ratios of C3depl-NHS and animal serum were changed. The key in the figure shows the % of porcine serum in SCM. The data show increased sensitivity with increasing amounts of C3depl-NHS in the incubation mixture, and near plateau of the reaction after about 60 min.

Conclusions:

There is inverse correlation between C3 consumption and the ratio of porcine serum added to the incubation mixture, in the 20-70% range.

The sensitivity of the assay increases with increasing amounts of C3depl-NHS added to the serum.

C3 consumption keeps rising until 1 hour incubation. Thereafter, the curve reaches plateau in the case of 45 and 70% serum, while it further rises in the case of 20% serum.

Optimal parameters for the pan-species C3 method in case of porcine serum are 20% test serum, 80% C3depl-NHS and 120 min incubation at 37° C.

Example 9: Demonstration of the Role of Zymosan in the C Activating and Specificity Converting Potency of C3-SCM in Individual and Pooled Pig Serum: Impact of Incubation Temperature Goal To ascertain that the zymosan-induced rise of SC5b-9 in pig serum is not due to elevated temperature (i.e. 37° C. vs. 4° C.), and that pooling of porcine sera has no major impact on C activation.

Materials and Methods

Similar studies as described in Example 3, except that incubation temperature was altered, and some sera were pooled for the assay. Pig serum was obtained from freshly drawn blood of pigs, while pooled pig serum was a mixture of sera obtained from freshly drawn bloods of 4 pigs.

Pooling was done before the measurement.

Results

The C3-SCM reagent lends sensitivity to the human SC5b-9 kit to measure C activation in pig serum solely by the presence of zymosan: rising the temperature to 37° C. from 4° C. does not reproduce the effect of zymosan. Also, pooling of pig serum led to smaller rise of SC5b-9 in response to zymosan, suggesting that may obscure potentially higher individual sensitivities of pigs to C activation by zymosan.

Conclusions

The C3-SCM reagent lends sensitivity to the human SC5b-9 kit to measure C activation in pig serum solely by the presence of zymosan: rising the temperature to 37° C. from 4° C. does not reproduce the effect of zymosan.

Pooling of pig serum may obscure potentially higher individual sensitivities of pigs to C activation by zymosan.

Example 10: Demonstration of the Use of Pan-Species C3 Method for the Measurement of C Activation by Liposomal Drugs, Doxil and Ambisome, in Rats In Vivo Goal To measure C activation in rats caused by known reactogenic liposomal drugs, liposomal doxorubicin (Doxil) and liposomal amphotericin-B (Ambisome).

Materials and Methods

Male Wistar rats (340-480 g) were anesthetized i.p. by Na-pentobarbital (Nembutal, 50 mg/kg) or thiobutabarbital (Inactin, 120 mg/kg). The left femoral artery and vein, left carotid artery, and right jugular vein were cannulated. Rats were anticoagualated with lepirudin (Refludan, 5 mg/kg), then injected i.v. with the C activator liposomes, Doxil and Ambisome. Blood samples were collected from the carotid artery at start (time 0) and at 1-3-5-10-30 min postinjection.

Results

Figure 4:
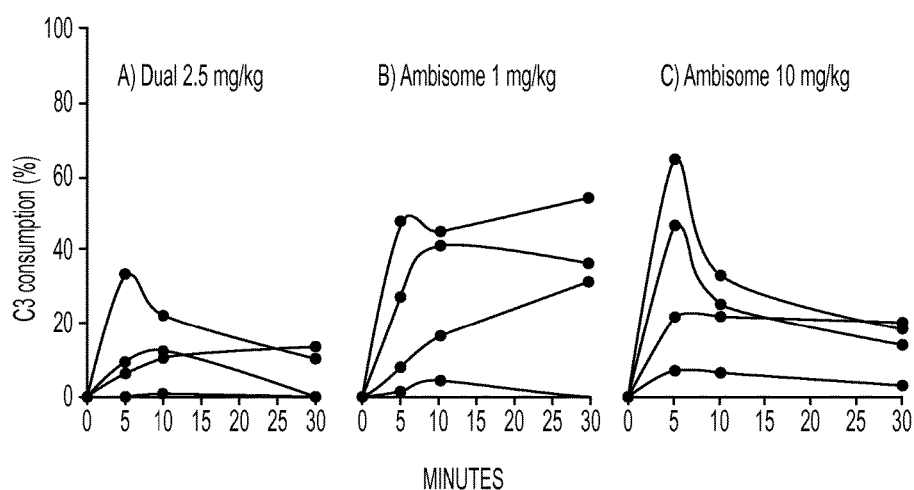
FIG. 4 shows complement activation by liposomes in rats in vivo, measured by the PS-C3 method in hirudinized plasma samples.

As shown in FIG. 4A, 3 out of 4 rats injected with Doxil (2.5 mg/kg phopsholipid/kg) displayed progressive C3 consumption on a time scale of minutes, with plateau reached after 5-10 min. FIGS. 4A and B show similar, but more expressed C consumption following injection of Ambisome (1 and 10 mg/kg, respectively), with visible differences in the heights and speeds of SC5b-9 rises, consistent with dose dependence of C response.

Conclusions

The pan-species C3 method can be used to quantitate C activation in rats by known reactogenic liposomal drugs.

The reactogenic dose is in the 1-10 mg phopsholipid/kg range.

Example 11: Demonstration of the Use of the Pan-Species C3 Method for the Measurement of C Activation by Zymosan and Cobra Venom Factor in Rats In Vivo Goal To measure C activation in rats caused by known reactogenic compounds, zymosan and cobra venom factor (CVF).

Materials and Methods

Similar experiments as described in Example 7, except that the rats were injected with 10 mg/kg zymosan or 12.5 U/kg CVF.

Results

Figure 5:
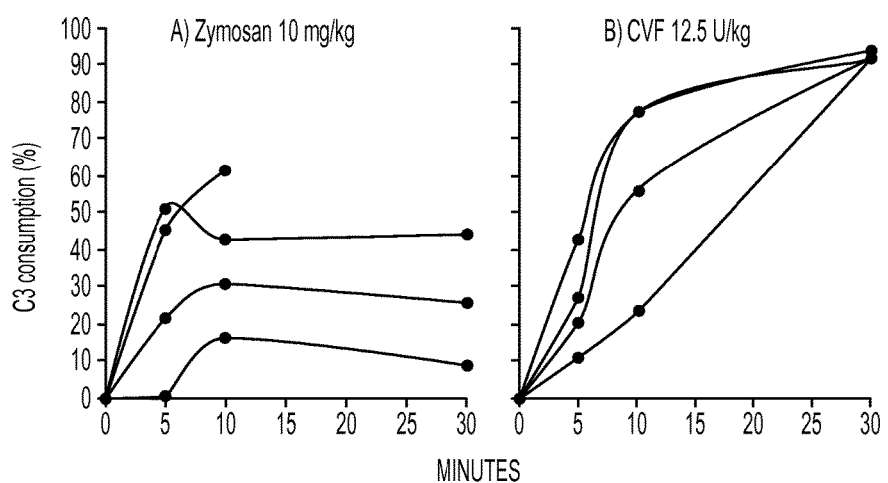
FIG. 5 shows C3 consumption by C activator substances in rats in vivo, measured by the PS-C3 method in hirudinized plasma samples.

FIGS. 5A and B show very similar reactions to zymosan and CVF as seen with liposomal drugs. The reaction to zymosan reached plateau after about 10 min maximum at 50-60% C3 consumption, while CVF consumed essentially all C3 within 30 min, following linear or sigmoid kinetics.

Conclusions

The PS-C3 method can be used to quantitate C activation in rats by known non-liposomal reactogenic agents as well, such as zymosan and cobra venom factor.

Example 12: Demonstration of the Use of Human C3a ELISA for the Measurement of C Activation in Rats by CVF In Vivo Goal To compare SC5b-9 and C3a as pan-species C3 method endpoints for the measurement of CVF-induced C activation in rats.

Materials and Methods

Similar experiments as described in Example 11, except that C activation was measured by Quidel's human SC5b-9 (A) and C3a kits (B). Rats were injected with 12.5 U/kg CVF.

Results

Figure 6:
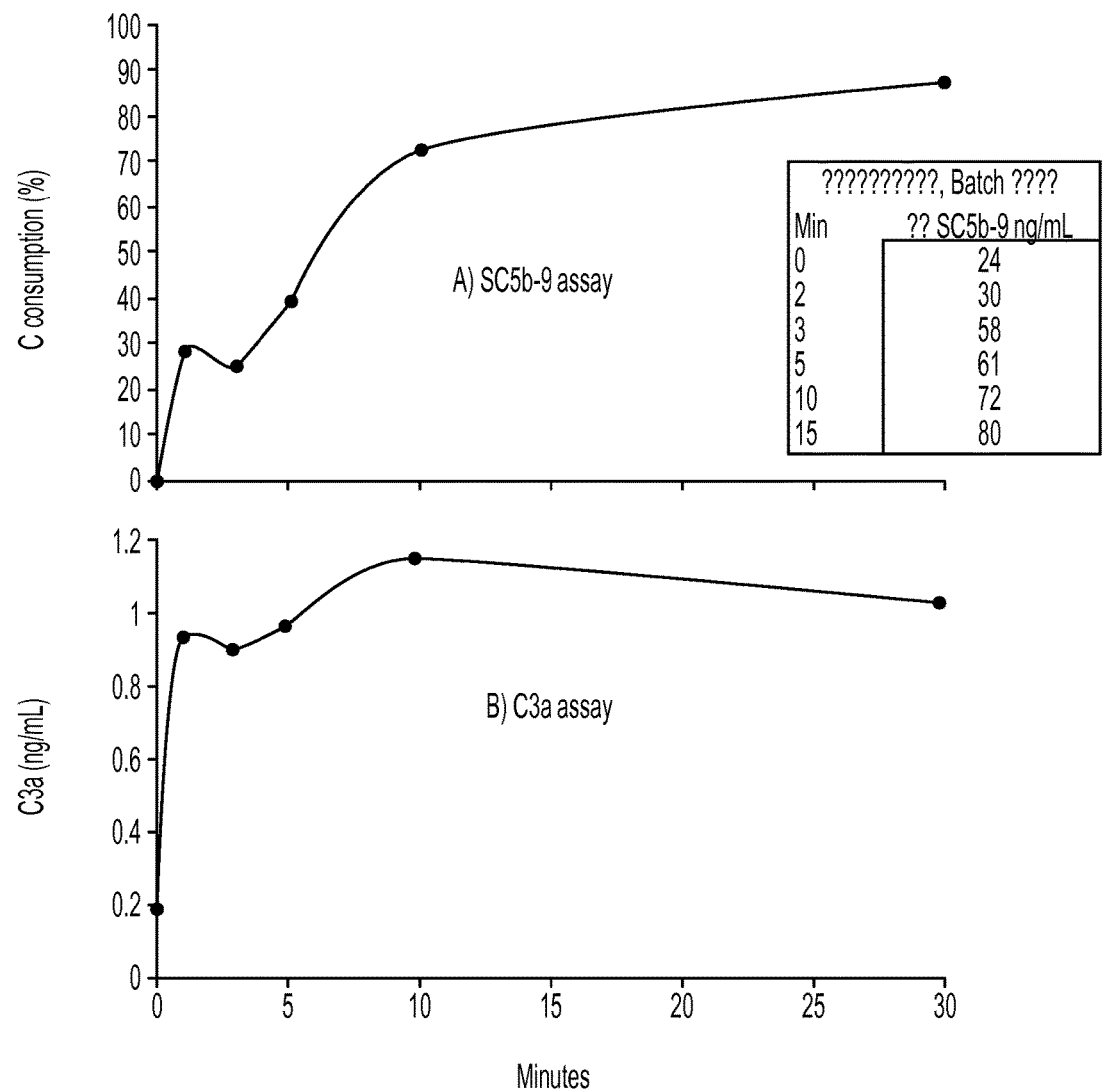
FIG. 6A shows C3 consumption by CVF in rats in vivo, measured by the PS-C3 method in hirudinized plasma samples.
FIG. 6B shows a similar experiment, except that in addition to SC5b-9, C3a were measured in the samples. The table insert in FIG. 6 shows the raw data from which the figure was constructed.

FIG. 6 shows that the activation curve obtained with the SC5b-9 kit is very similar to the results shown in FIG. 5B, thus confirming the use of SC5b-9 as assay endpoint. Interestingly, human C3a was also elevated in the reaction mixture, as measured by Quidel's C3a kit. This observation cannot be attributed to cross reaction of rat C3a with anti-human C3a antibodies in the human kit, since in independent studies we have unambiguously shown the lack of cross reaction.

Conclusions

The pan-species C3 method can also utilize C3a as endpoint.

The exact explanation of C3a rise during the pan-species C3 method is not clear.

The conditions under which C3a can be used to measure C activation in animals remains to be further explored.

Example 13: Demonstration of the Use of Pan-Species C3 Method to Detect C Activation in Pigs In Vivo Goal To use the pan-species C3 method in order to measure C activation in pigs caused by zymosan.

Materials and Methods

Materials and Animals

Zymosan was from Sigma. Male, castrated Yorkshire pigs weighing 12-25 kg were obtained from a local Vendor.

Surgery and Instrumentation

After premedication with ketamine (500 mg i.m.), an ear vein was canulated and the animals were anesthetized with pentobarbital (5-20 mg/kg i.v.). Intubation was carried out with 6.5 Fr tracheal tube to maintain free airway, and to enable controlled ventilation if needed. A catheter was introduced into the left femoral artery for systemic arterial pressure (SAP) measurement and blood sampling. An intravenous line was established at the left internal jugular or femoral vein for fluid supplementation with saline, and administration of subsequent doses of the anaesthetics as necessary. To measure pulmonary arterial blood pressure (PAP) a Swan-Ganz catheter was introduced into the right external jugular vein and led into the pulmonary artery via the right atrium and ventricle. SAP, PAP and standard Einthoven's ECG leads I, II and III were recorded continuously with ADinstrument LabChart Pro software at a sampling rate of 2000 Hz. Zymosan (0.5 mg/kg) was injected into the pulmonary artery as bolus.

Measurement of Pig C3 by Human SC5b-9

Aliquots (10 µL) from the plasma samples taken at different times (0, 1, 2, 3, 5, 10 min) following the injection of zymosan in pigs was mixed with an equivolume of SCM (10 µL), and the mixture was incubated at 37° C. for 30 min. The reaction was stopped by adding 10 Vol sample diluents complemented with 10 mM EDTA, and the samples were measured using Quidel's SC5b-9 kit according to the manufacturers' instructions.

Results

Figure 7:
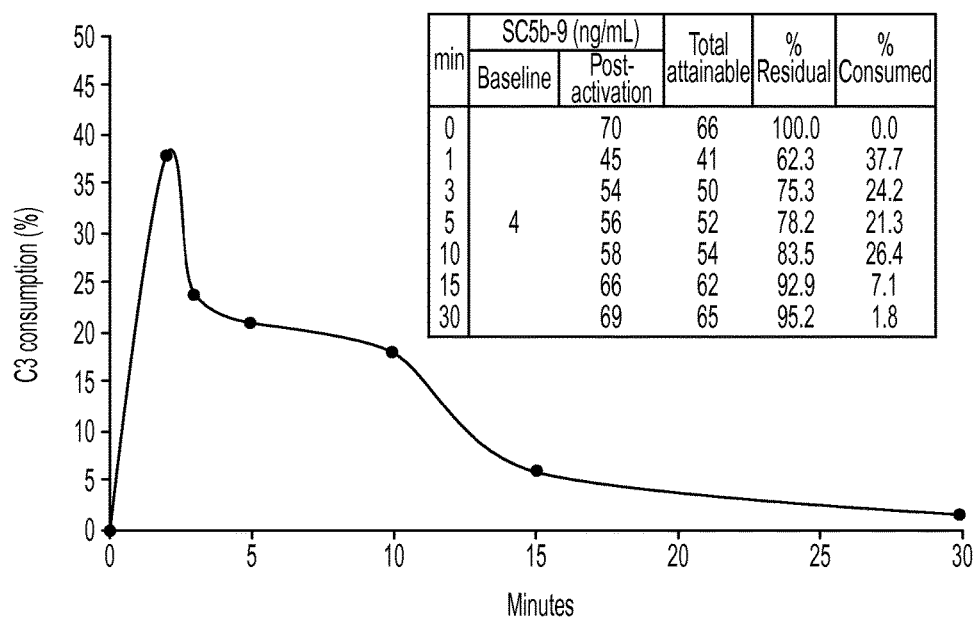
FIG. 7 shows C3 consumption by zymosan in a pig, measured by the PS-C3 method in hirudinized plasma samples. The table insert in FIG. 7 shows the raw data from which the figure was constructed.

As shown in FIG. 7, 2.5 mg/kg zymosan caused very similar reaction in the pig as seen in rats, with the exception that the reaction was faster (peaked at 3 min at 35% C3 consumption and plasma C3 levels returned to baseline earlier than in rats (within 30 min).

Conclusions

The pan-species C3 method can be used to quantitate C activation in pigs by zymosan.

The reaction is similar to that seen in rats, except that it is induced by a lower dose of zymosan, and the kinetics of changes are faster, the return to baseline is more complete.

Example 14: Demonstration of the Use of Pan-Species C3 Method to Detect C Activation in Dogs In Vivo Goal To use the pan-species C3 method in order to measure C activation in dogs in vivo, caused by reactogenic anticancer drugs Materials and Methods Dog serum was obtained from B. Kohn, Clinic of Small Animals, Faculty of Veterinary Medicine, Freie Universitat Berlin—Germany Materials and animal doses of drugs applied were:
Vincristine: 0.5 mg/kg—Bolus
Carboplatin 280 mg/m2—infusion over 20 min
Sample collection: before and 30 min afterinjection/infusion Results Vincristine and carboplatin caused substantial (20-57%) C consumption in dog plasma in vivo, measured by the human SC5b-9 kit.

Conclusions

The pan-species C3 method can be used to quantitate C activation in dogs by reactogenic anticancer drugs.

Unlike in rats, C3a decreases as a consequence of drug exposure, which is consistent with C activation.

REFERENCES

1. Szebeni J, editor. The Complement System: Novel Roles in Health and Disease. Boston: Kluwer; 2004.
2. Leslie M. The new view of complement. Science. 2012; 337:1034-7.
3. Chaplin H, Jr. Review: the burgeoning history of the complement system 1888-2005. Immunohematology/American Red Cross. 2005; 21(3):85-93. Epub 2005 Sep. 24.
4. Szebeni J, Fontana J L, Wassef N M, Mongan P D, Morse D S, Dobbins D E, et al. Hemodynamic changes induced by liposomes and liposome-encapsulated hemoglobin in pigs: a model for pseudo-allergic cardiopulmonary reactions to liposomes. Role of complement and inhibition by soluble CR1 and anti-C5a antibody. Circulation. 1999; 99:2302-9.
5. Szebeni J. Complement activation-related pseudoallergy: a new class of drug-induced immune toxicity. Toxicology. 2005; 216:106-21.
6. Olmstead M P, Povitzky O R. The Complement Fixation Reactions of the Bordet-Gengou *Bacillus*. The Journal of medical research. 1916; 33(3):379-92. Epub 1916 Jan. 1.
7. Muller-Eberhard H J, Gotze 0. C3 proactivator convertase and its mode of action. The Journal of experimental medicine. 1972; 135(4):1003-8. Epub 1972 Apr. 1.
8. Johnson U. Properdin acting as a C3 convertase. Acta pathologica et microbiologica Scandinavica Section B: Microbiology and immunology. 1974; 82(6):914-6. Epub 1974 Dec. 1.
9. Fearon D T, Austen K F. Properdin: binding to C3b and stabilization of the C3b-dependent C3 convertase. The Journal of experimental medicine. 1975; 142(4):856-63. Epub 1975 Oct. 1.
10. Amos N, Sissons J G, Girard J F, Lachmann P J, Peters D K. The cofactors required by C3 nephritic factor to generate a C3 convertase in vitro. Clinical and experimental immunology. 1976; 24(3):474-82. Epub 1976 Jun. 1.
11. Daha M R, Fearon D T, Austen K F. Formation in the presence of C3 nephritic factor (C3NeF) of an alternative pathway C3 convertase containing uncleaved B. Immunology. 1976; 31(5):789-96. Epub 1976 Nov. 1.
12. Daha M R, Fearon D T, Austen K F. C3 requirements for formation of alternative pathway C5 convertase. J Immunol. 1976; 117(2):630-4. Epub 1976 Aug. 1.
13. Medicus R G, Gotze O, Muller-Eberhard H J. Alternative pathway of complement: recruitment of precursor properdin by the labile C3/C5 convertase and the potentiation of the pathway. The Journal of experimental medicine. 1976; 144(4):1076-93. Epub 1976 Oct. 1.
14. Pangburn M K, Muller-Eberhard H J. Complement C3 convertase: cell surface restriction of beta1H control and generation of restriction on neuraminidase-treated cells. Proceedings of the National Academy of Sciences of the United States of America. 1978; 75(5):2416-20. Epub 1978 May 1.
15. Gigli I, Fujita T, Nussenzweig V. Modulation of the classical pathway C3 convertase by plasma proteins C4 binding protein and C3b inactivator. Proceedings of the National Academy of Sciences of the United States of America. 1979; 76(12):6596-600. Epub 1979 Dec. 1.
16. Lesavre P H, Hugli T E, Esser A F, Muller-Eberhard H J. The alternative pathway C3/C5 convertase: chemical basis of factor B activation. J Immunol. 1979; 123(2): 529-34. Epub 1979 Aug. 1.
17. Sobel A T, Cooper N R, Schreiber R D. Activation of the classical complement pathway by nephritic factor bound to the alternative pathway C3/C5 convertase. J Immunol. 1979; 122(1):34-8. Epub 1979 Jan. 1.
18. Isenman D E, Podack E R, Cooper N R. The interaction of C5 with C3b in free solution: a sufficient condition for cleavage by a fluid phase C3/C5 convertase. J Immunol. 1980; 124(1):326-31. Epub 1980 Jan. 1.
19. Kerr M A. The human complement system: assembly of the classical pathway C3 convertase. The Biochemical journal. 1980; 189(1):173-81. Epub 1980 Jul. 1.
20. Strunk R C, Giclas P C. Modulation of the activity of the classical complement pathway C3 convertase by surface-bound C3 or C5. J Immunol. 1980; 124(2):520-6. Epub 1980 Feb. 1.
21. Pangburn M K, Schreiber R D, Muller-Eberhard H J. Formation of the initial C3 convertase of the alternative complement pathway. Acquisition of C3b-like activities by spontaneous hydrolysis of the putative thioester in native C3. The Journal of experimental medicine. 1981; 154(3):856-67. Epub 1981 Sep. 1.
22. DiScipio R G. The activation of the alternative pathway C3 convertase by human plasma kallikrein. Immunology. 1982; 45(3):587-95. Epub 1982 Mar. 1.
23. Smith C A, Vogel C W, Muller-Eberhard H J. Ultrastructure of cobra venom factor-dependent C3/C5 convertase and its zymogen, factor B of human complement. The Journal of biological chemistry. 1982; 257(17):9879-82. Epub 1982 Sep. 10.
24. Brown E J, Ramsey J, Hammer C H, Frank M M. Surface modulation of classical pathway activation: C2 and C3 convertase formation and regulation on sheep, guinea pig, and human erythrocytes. J Immunol. 1983; 131(1):403-8. Epub 1983 Jul. 1.
25. Fishelson Z, Muller-Eberhard H J. The C3/C5 convertase of the alternative pathway of complement: stabilization and restriction of control by lanthanide ions. Molecular immunology. 1983; 20(3):309-15. Epub 1983 Mar. 1.
26. Fishelson Z, Pangburn M K, Muller-Eberhard H J. C3 convertase of the alternative complement pathway. Demonstration of an active, stable C3b, Bb (Ni) complex. The Journal of biological chemistry. 1983; 258(12):7411-5. Epub 1983 Jun. 25.
27. Loos M, Heinz H P. Generation of the classical pathway C3 convertase (EAC4b2a) by proteolytic enzymes. Acta pathologica, microbiologica, et immunologica Scandinavica Supplement. 1984; 284:67-74. Epub 1984 Jan. 1.
28. Gigli I, Sorvillo J, Halbwachs-Mecarelli L. Regulation and deregulation of the fluid-phase classical pathway C3 convertase. J Immunol. 1985; 135(1):440-4. Epub 1985 Jul. 1.
29. Strunk R C, Webster R O. Inhibition of cleavage of the third component of human complement (C3) by its small cleavage fragment, C3a: inhibition occurs with the classical-pathway, but not the alternative-pathway, C3 convertase. Molecular immunology. 1985; 22(1):37-43. Epub 1985 Jan. 1.
30. Pangburn M K, Muller-Eberhard Hi. The C3 convertase of the alternative pathway of human complement. Enzymic properties of the bimolecular proteinase. The Biochemical journal. 1986; 235(3):723-30. Epub 1986 May 1.
31. Fishelson Z, Muller-Eberhard H J. C3 convertase of the human alternative pathway of complement: modulation of enzyme activity and stability by mouse monoclonal antibodies to Bb. European journal of immunology. 1987; 17(2):303-4. Epub 1987 Feb. 1.
32. Inagi R, Miyata T, Maeda K, Sugiyama S, Miyama A, Nakashima I. FUT-175 as a potent inhibitor of C5/C3 convertase activity for production of C5a and C3a. Immunology letters. 1991; 27(1):49-52. Epub 1991 Jan. 1.
33. Masaki T, Matsumoto M, Yasuda R, Levine R P, Kitamura H, Seya T. A covalent dimer of complement C4b serves as a subunit of a novel C5 convertase that involves no C3 derivatives. J Immunol. 1991; 147(3):927-32. Epub 1991 Aug. 1.
34. Naito A, Okada H. Stability of C3 convertase in the rat classical complement pathway. Microbiology and immunology. 1997; 41(8):621-4. Epub 1997 Jan. 1.
35. Hourcade D E, Mitchell L M, Medof M E. Decay acceleration of the complement alternative pathway C3 convertase. Immunopharmacology. 1999; 42(1-3):167-73. Epub 1999 Jul. 17.
36. Krych-Goldberg M, Hauhart R E, Porzukowiak T, Atkinson J P. Synergy between two active sites of human complement receptor type 1 (CD35) in complement regulation: implications for the structure of the classical pathway C3 convertase and generation of more potent inhibitors. J Immunol. 2005; 175(7):4528-35. Epub 2005 Sep. 24.
37. Harris C L, Pettigrew D M, Lea S M, Morgan B P. Decay-accelerating factor must bind both components of the complement alternative pathway C3 convertase to mediate efficient decay. J Immunol. 2007; 178(1):352-9. Epub 2006 Dec. 22.
38. Krishnan V, Xu Y, Macon K, Volanakis J E, Narayana S V. The crystal structure of C2a, the catalytic fragment of classical pathway C3 and C5 convertase of human complement. Journal of molecular biology. 2007; 367(1): 224-33. Epub 2007 Jan. 20.
39. Moller-Kristensen M, Thiel S, Sjoholm A, Matsushita M, Jensenius J C. Cooperation between MASP-1 and MASP-2 in the generation of C3 convertase through the MBL pathway. International immunology. 2007; 19(2): 141-9. Epub 2006 Dec. 22.
40. Krishnan V, Xu Y, Macon K, Volanakis J E, Narayana S V. The structure of C2b, a fragment of complement component C2 produced during C3 convertase formation. Acta crystallographica Section D, Biological crystallography. 2009; 65(Pt 3):266-74. Epub 2009 Feb. 25.
41. Rawal N, Rajagopalan R, Salvi V P. Stringent regulation of complement lectin pathway C3/C5 convertase by C4b-binding protein (C4BP). Molecular immunology. 2009; 46(15):2902-10. Epub 2009 Aug. 8.
42. Roumenina L T, Jablonski M, Hue C, Blouin J, Dimitrov J D, Dragon-Durey M A, et al. Hyperfunctional C3 convertase leads to complement deposition on endothelial cells and contributes to atypical hemolytic uremic syndrome. Blood. 2009; 114(13):2837-45. Epub 2009 Jul. 9.
43. Ricklin D. Manipulating the mediator: modulation of the alternative complement pathway C3 convertase in health, disease and therapy. Immunobiology. 2012; 217(11): 1057-66. Epub 2012 Sep. 12.
44. Holmquist E, Okroj M, Nodin B, Jirstrom K, Blom A M. Sushi domain-containing protein 4 (SUSD4) inhibits complement by disrupting the formation of the classical C3 convertase. FASEB journal: official publication of the Federation of American Societies for Experimental Biology. 2013; 27(6):2355-66. Epub 2013 Mar. 14.
45. Janeway C A J. Immunobiology: The Immune System in Health and Disease. 5th edition. Janeway C A J, Travers P, Walport M, editors. New York: Garland Science; 2001.
46. Yeap S K, Omar A R, Ho W Y, Beh B K, Ali A M, Alitheen N B. Rhaphidophora korthalsii modulates peripheral blood natural killer cell proliferation, cytokine secretion and cytotoxicity. BMC complementary and alternative medicine. 2013; 13:145. Epub 2013 Jun. 27.
47. Lopes R D, Lokhnygina Y, Hasselblad V, Newby K L, Yow E, Granger C B, et al. Methods of creatine kinase-M B analysis to predict mortality in patients with myocardial infarction treated with reperfusion therapy. Trials. 2013; 14:123. Epub 2013 Jun. 21.
48. Ho J Y, Hsu R J, Wu C L, Chang W L, Cha T L, Yu D S, et al. Ovatodiolide Targets beta-Catenin Signaling in Suppressing Tumorigenesis and Overcoming Drug Resistance in Renal Cell Carcinoma. Evidence-based complementary and alternative medicine: eCAM. 2013; 2013:161628. Epub 2013 Jun. 20.
49. Wang C W, Chan C L, Ho R T, Tsang H W, Chan C H, Ng S M. The effect of qigong on depressive and anxiety symptoms: a systematic review and meta-analysis of randomized controlled trials. Evidence-based complementary and alternative medicine: eCAM. 2013; 2013: 716094. Epub 2013 Jun. 14.
50. van Diepen S, Vavalle J P, Newby L K, Clare R, Pieper K S, Ezekowitz J A, et al. The Systemic Inflammatory Response Syndrome in Patients With ST-Segment Elevation Myocardial Infarction. Critical care medicine. 2013. Epub 2013 Jun. 14.
51. Zarzycki-Siek J, Norris M H, Kang Y, Sun Z, Bluhm A P, McMillan I A, et al. Elucidating the *Pseudomonas aeruginosa* Fatty Acid Degradation Pathway: Identification of Additional Fatty Acyl-CoA Synthetase Homologues. PloS one. 2013; 8(5):e64554. Epub 2013 Jun. 6.
52. Yu H, Zhang W L, Ding X, Zheng K Y, Ho C M, Tsim K W, et al. Optimizing combinations of flavonoids deriving from astragali radix in activating the regulatory element of erythropoietin by a feedback system control scheme. Evidence-based complementary and alternative medicine: eCAM. 2013; 2013:541436. Epub 2013 Jun. 6.
53. Lee S Y, Li M H, Shi L S, Chu H, Ho C W, Chang T C. *Rhodiola crenulata* Extract Alleviates Hypoxic Pulmonary Edema in Rats. Evidence-based complementary and alternative medicine: eCAM. 2013; 2013:718739. Epub 2013 May 28.
54. Yeap S K, Mohd Yusof H, Mohamad N E, Beh B K, Ho W Y, Ali N M, et al. In Vivo Immunomodulation and Lipid Peroxidation Activities Contributed to Chemoprevention Effects of Fermented Mung Bean against Breast Cancer. Evidence-based complementary and alternative medicine: eCAM. 2013; 2013:708464. Epub 2013 May 28.
55. Cheng C C, Huang C F, Ho A S, Peng C L, Chang C C, Mai F D, et al. Novel targeted nuclear imaging agent for gastric cancer diagnosis: glucose-regulated protein 78 binding peptide-guided 111In-labeled polymeric micelles. International journal of nanomedicine. 2013; 8:1385-91. Epub 2013 May 1.
56. Autoimmunoregulation and autoimmune disease. Dedicated to the memory of Jules Bordet (1870-1961), pioneer in immunology and complement research. Concepts in immunopathology. 1987; 4:1-303. Epub 1987 Jan. 1.
57. Coombs R R, Wilson A B, Lachmann P J. The coagglutination phenomenon of Bordet and Gengou involves a reaction between antibody-aggregated fourth component of complement and a receptor on guniea pig red cells. International archives of allergy and applied immunology. 1980; 61(4):371-9. Epub 1980 Jan. 1.
58. Alieva S G, Desiatchikova A V, Baluiants E S, Alimov Kh A, Kogai E A. [Bordet-Gengou reaction and cold complement fixation reaction data in the diagnosis of gonorrhea]. Vestnik dermatologii i venerologii. 1979(8): 60-3. Epub 1979 Aug. 1. Materialy po reaktsii Borde-Zhangu i reaktsii sviazyvaniia komplementa na kholodu pri diagnostike gonorei.
59. Linder A, Brun R. [Statistical control of a laboratory method; distribution & frequency of autodeviation of complement in the Bordet-Wassermann reaction]. Dermatologica. 1957; 115(3):298-303. Epub 1957 Sep. 1. Controle statistique d'une methode de laboratoire; repartition et frequence de l'autodeviation du complement dans la reaction de Bordet-Wassermann.
60. Ade G, Brun R. [Statistical researches on anti-complement power in Bordet-Wassermann reaction]. Dermatologica. 1955; 111(6):366-81. Epub 1955 Dec. 1. Recherches statistiques sur l'autodeviation du complement dans la reaction de Bordet-Wassermann.
61. Yang Y, Li Q, Ju Z, Huang J, Zhou L, Li R, et al. Three novel single-nucleotide polymorphisms of complement component 4 gene (C4A) in Chinese Holstein cattle and their associations with milk performance traits and CH50. Veterinary immunology and immunopathology. 2012; 145(1-2):223-32. Epub 2011 Dec. 14.
62. Ahmadinejad Z, Bagherian H, Atarord L, Soodbakhsh A, Saheli G. Lymphocyte subsets, immunoglobulin levels, complement activity CH50, and phagocytic peroxide production in 19 Iranian patients with first episode of bacterial meningitis. Journal of microbiology, immunology, and infection=Wei mian yu gan ran za zhi. 2011; 44(2): 83-7. Epub 2011 Mar. 29.
63. Costabile M. Measuring the 50% haemolytic complement (CH50) activity of serum. Journal of visualized experiments: JoVE. 2010(37). Epub 2010 Mar. 31.
64. Qiu H, Liu S, Xie C, Long J, Feng Z. Regulating immunity and inhibiting tumor growth by the recombinant peptide sPD-1-CH50. Anticancer research. 2009; 29(12):5089-94. Epub 2010 Jan. 2.
65. Martens H A, Zuurman M W, de Lange A H, Nolte I M, van der Steege G, Navis G J, et al. Analysis of C1q polymorphisms suggests association with systemic lupus erythematosus, serum C1q and CH50 levels and disease severity. Annals of the rheumatic diseases. 2009; 68(5): 715-20. Epub 2008 May 28.
66. Xu H, Kitano E, Sato Y, Kobayashi C, Firdawes S, Kitamura H, et al. Studies of monkey complement: measurement of cynomolgus monkey CH50, ACH50, C4, C2 and C3. Xenotransplantation. 2008; 15(1):14-9. Epub 2008 Mar. 13.
67. Yu Z R, Zhang G M, Li D, Liu Y, Geng H, Xiao H, et al. [The inhibitory effect of recombinant polypeptide CH50 of fibronectin on invasion and angiogenesis of tumors]. Zhonghua zhong liu za zhi [Chinese journal of oncology]. 2006; 28(11):815-9. Epub 2007 Apr. 10.
68. Wei J, Xiong Y. Inhibitory effect of recombinant fibronectin polypeptide CH50 on invasion and metastasis of melanoma B16 cells. Journal of Huazhong University of Science and Technology Medical sciences=Hua zhong ke ji da xue xue bao Yi xue Ying De wen ban=Huazhong keji daxue xuebao Yixue Yingdewen ban. 2007; 27(1): 17-9. Epub 2007 Mar. 30.
69. Wu Z, Chen Z, Ye Z, Zhang J, Ye S, Zhang G, et al. Effects of gene tranfection with CH50 polypeptide on the invasion ability of bladder cancer cell line BIU-87. Journal of Huazhong University of Science and Technology Medical sciences=Hua zhong ke ji da xue xue bao Yi xue Ying De wen ban=Huazhong keji daxue xuebao Yixue Yingdewen ban. 2005; 25(3):320-2, 38. Epub 2005 Oct. 6.
70. Kitano E, Kitamura H. [Immunologic tests: CH50]. Nihon rinsho Japanese journal of clinical medicine. 2005; 63 Suppl 7:47-51. Epub 2005 Aug. 23.
71. Feng Z, Zhang G, Zhang H, Li D, Zhou Y. Inhibitory effect of recombinant FN polypeptide CH50 on the metastasis and tumor growth. Journal of Tongji Medical University=Tong ji yi ke da xue xue bao. 1999; 19(4): 249-52, 79. Epub 2003 Aug. 27.
72. Zhang G, Feng Z, Li D, Cao H, Zhang H. Augmentation of recombinant CH50 polypeptide on the function of macrophages of mice during chemotherapy. Journal of Tongji Medical University=Tong ji yi ke da xue xue bao. 2000; 20(2):97-9. Epub 2003 Jul. 9.
73. Feng Z, Huang B, Zhang G, Li D, Zhang H. Construction of eukaryotic expressing vector pCH503 of CH50 and its chemotaxis and anti-tumor function by expression in vivo in mice. Journal of Tongji Medical University=Tong ji yi ke da xue xue bao. 2000; 20(2):92-6. Epub 2003 Jul. 9.
74. Zhu M, Zeng Y, Jiang L, Huang P, Wu Z. [Effects on the amount of total hemolytic complement levels (CH50) and immunoglobulin in serum induced by the implantation of biomaterials into rats]. Sheng wu yi xue gong cheng xue za zhi=Journal of biomedical engineering=Shengwu yixue gongchengxue zazhi. 1999; 16(3):275-8. Epub 2003 Jan. 30.
75. Uchibori E, Kitano E, Tsuji T, Kitamura H. [Study on CH50 levels in factor D-depleted serum]. Rinsho byori The Japanese journal of clinical pathology. 2002; 50(8): 815-9. Epub 2002 Oct. 11.
76. Wozniakowska-Gesicka T, Wisniewska-Ligier M, Kups J. Effect of IFN-alpha on total haemolytic activity of CH50 complement system and C3, C4 levels in children with chronic hepatitis C. Medical science monitor: international medical journal of experimental and clinical research. 2001; 7 Suppl 1:202-6. Epub 2002 Sep. 6.
77. Zhang H, Feng Z, Zhang G. [The inhibitory effect of recombinant fibronectin polypeptide CH50 on the growth of B16 melanoma]. Zhonghua zhong liu za zhi [Chinese journal of oncology]. 1999; 21(6):416-8. Epub 2002 Jan. 5.
78. Li D, Feng Z, Ye S, Zhang G, Zhang H, Huang B, et al. Construction and expression of eukaryotic expressing vector pCH510 of polypeptide CH50 and its chemotaxis and antitumor function by in vivo transfection. Journal of Tongji Medical University=Tong ji yi ke da xue xue bao. 2001; 21(1):1-5. Epub 2001 Aug. 29.
79. Zhang G M, Feng Z H, Li D, Zhang H. Comparison of effects of CH50 on macrophage activation and its antitumor activity with those of lipopolysaccharides. Acta pharmacologica Sinica. 2000; 21(6):567-70. Epub 2001 May 22.
80. Zhang G, Feng Z, Li D, Zhang H. Effect of polypeptide CH50 on macrophage activation in vivo and anti-tumor function. Journal of Tongji Medical University=Tong ji yi ke da xue xue bao. 2000; 20(3):190-3. Epub 2001 Feb. 24.
81. Shecterle L M, Wetherall N, St Cyr J A. Effects on C3 and CH50 levels during and following extracorporeal whole body hyperthermia. The Journal of extra-corporeal technology. 1999; 31(4):191-4. Epub 2000 Aug. 1.
82. Zhang G, Feng Z, Zhang H, Fan Q, Li D. Augmentation of recombinant fibronectin polypeptide CH50 on the antitumor function of macrophages. Journal of Tongji Medical University=Tong ji yi ke da xue xue bao. 1998; 18(1):5-9. Epub 2000 May 12.
83. Fan Q, Feng Z H, Zhang G M, Zhang H, Cao H Q. Effect of recombinant human fibronectin polypeptide CH50 on growth and metastasis of melanoma. Zhongguo yao li xue bao=Acta pharmacologica Sinica. 1999; 20(2):175-8. Epub 1999 Aug. 7.
84. Ceccon M E, Diniz E M, Carneiro-Sampaio M M, Arslanian C, Diogo C L, Ramos J L, et al. [Immunological behavior (IgG, IgM, IgA) and total complement (CH50) of newborns infants with risk factors for early onset sepsis. Comparative analysis of newborns with and without infection]. Revista do Hospital das Clinicas. 1998; 53(6):303-10. Epub 1999 Jul. 22. Comportamento imunologico (IgG, IgM, IgA) e complemento total (CH 50) de recem-nascidos corn fatores de risco para sepse precoce. Analise comparativa entre recem-nascidos corn e sem infeccao.
85. Shimada A, Nagata H, Kojima H, Yamate A. [Significance of plasma fibronectin and CH50 determination in the evaluation of tissue responses of medical materials]. Nihon Geka Gakkai zasshi. 1998; 99(11):794. Epub 1999 Apr. 13.
86. Souda N, Fujioka T, Kondou Y, Baba S, Hiwatashi S, Sibayama A, et al. [Studies on the conditions of blood sampling and storage for the liposome-based CH50 assay]. Rinsho byori The Japanese journal of clinical pathology. 1998; 46(10):1049-55. Epub 1998 Nov. 17.
87. Zhang G, Feng Z, Zhang H, Li D, Fan Q. Comparative study on the inhibitory effect of recombinant F N polypeptide CH50 and CH56 on the metastasis of melanoma cells. Journal of Tongji Medical University=Tong ji yi ke da xue xue bao. 1997; 17(3):129-31. Epub 1997 Jan. 1.
88. Yoshida H, Nagai T, Kato Y. [Immune serum tests. Sampling for complement tests—determination of serum complement hemolytic activity (CH50) and problems associated with handling of samples]. Rinsho byori The Japanese journal of clinical pathology. 1996; Suppl 103: 221-6. Epub 1996 Nov. 1.
89. Ibe M, Kuriyama T, Mori M, Mitsuda T, Aihara Y, Yokota S. [Evaluation of serum C3 and CH50 levels as markers of disease-activity and indicators of efficacy of treatment of lupus nephritis in childhood]. Ryumachi [Rheumatism]. 1994; 34(4):715-24. Epub 1994 Aug. 1.
90. Anil S, Beena V T, Remani P, Mysore J, Vijayakumar T. Total hemolytic complement (CH50) and its fractions C3 and C4 in the sera of patients with localized juvenile periodontitis. Annals of dentistry. 1993; 52(1):18-20. Epub 1993 Jan. 1.
91. Ceroni M, Camana C, Giardini G, Savoldi F, Fumagalli M. Evaluation of zymosan-induced complement activation by CH50 test. Il Farmaco; edizione pratica. 1986; 41(4):147-54. Epub 1986 Apr. 1.
92. Infortuna M, Barberio G, Magazzu G, Gattarello A, Leonardi M S. [Preliminary evaluation of the effect of total complement (CH50) on blood and duodenal juice in children with malabsorption syndrome]. Minerva pediatrica. 1985; 37(11-12):439-41. Epub 1985 Jun. 30. Valutazioni preliminari sul comportamento del complemento totale (CH50) su siero e succo duodenale di soggetti di eta pediatrica affetti da sindrome da malassorbimento.

93. Yoshida H, Satoh K, Ohkubo Y, Takagi T, Saito K, Morito T, et al. Useful marker of hemolytic complement activity (CH50) for the diagnosis of severe acute hepatitis. Fukushima journal of medical science. 1985; 31(1):43-8. Epub 1985 Jun. 1.

94. Woodfork K, Burrell R. A BASIC computer program for calculation of CH50 values by probit analysis. Computers in biology and medicine. 1985; 15(3):133-6. Epub 1985 Jan. 1.

95. Fetterhoff T J, McCarthy R C. A micromodification of the CH50 test for the classical pathway of complement. Journal of clinical & laboratory immunology. 1984; 14(4):205-8. Epub 1984 Aug. 1.

96. Blann A D, Lewin I, Bacon P A. Development and evaluation of a rapid, semi-automatic micro-method for CH50 estimation using a computer program. Immunological investigations. 1990; 19(2):109-18. Epub 1990 Apr. 1.

97. Ning J, Chang T M. Whole complement hemolytic activity (CH50) following infusion of stroma-free and polyhemoglobin solutions in rats. Biomaterials, artificial cells, and artificial organs. 1990; 18(2):203-17. Epub 1990 Jan. 1.

98. Jin A, Chen P, Ke X, Yu M, Fan L, Zhang N, et al. [Observation of the third component of complement (C3) and total hemolytic complement (CH50) in serum with SLE]. Zhongguo yi xue ke xue yuan xue bao Acta Academiae Medicinae Sinicae. 1982; 4(5):322-3. Epub 1982 Oct. 1.

99. Kaneda Y. [Development of complement system during infantile period. Part 3. Determination of total hemolytic complement activities (CH50) and complement protein levels in newborn sera, with special reference to gestational age and birth weight]. Arerugi=[Allergy]. 1982; 31(9):985-94. Epub 1982 Sep. 1.

100. Gupte S, Sabharwal U, Chugh T D. Serum CH50 and C'3 levels in malaria. The Indian journal of medical research. 1982; 76:130-3. Epub 1982 Jul. 1.

101. Fujiwara S. [Complement hemolytic activity (CH50), C3 and C4 levels in serum and plasma of the patients with various liver diseases (author's transl)]. Nihon Shokakibyo Gakkai zasshi=The Japanese journal of gastro-enterology. 1981; 78(2):190-9. Epub 1981 Feb. 1.

102. Nagaki K, Hiramatsu S, Inai S, Sasaki A. The effect of aging on complement activity (CH50) and complement protein levels. Journal of clinical & laboratory immunology. 1980; 3(1):45-50. Epub 1980 Jan. 1.

103. Qiu S, Liu Z, Hou L, Li Y, Wang J, Wang H, et al. Complement activation associated with polysorbate 80 in beagle dogs. International immunopharmacology. 2013; 15(1):144-9. Epub 2012 Nov. 20.

104. Moghimi S M, Wibroe P P, Szebeni J, Hunter A C. Surfactant-mediated complement activation in beagle dogs. International immunopharmacology. 2013; 17(1): 33-4. Epub 2013 Jun. 6.

105. Jin A. [Clinical observations on C3 and CH50 in the serum of patients with systemic lupus erythematosus]. Zhonghua yi xue za zhi. 1984; 64(1):36-8. Epub 1984 Jan. 1.

106. Kandrac M, Kunay M, Trejbal D, Machanova Y, Merstenova E, Halko N. [Complement CH50 and C3 complement fraction levels in autoimmune thyroiditis (author's transl)]. Casopis lekaru ceskych. 1979; 118(24): 760-3. Epub 1979 Jun. 18. Hladina komplementu CH50 a C 3 frakcie komplementu u autoimunnych tyreoiditid.

107. Ishikawa Y. [Relationship between serum complement titer (CH50), immune adherence (IA), beta-1-A-globulin, transferrin, IgA, IgM and IgG in SLE]. Arerugi=[Allergy]. 1969; 18(12):966-72. Epub 1969 Dec. 1.

108. Arata M. [Studies on human serum complement. 2. Epidemiological study on sera with low levels of CH50 based on a study of a rural area]. Arerugi=[Allergy]. 1969; 18(4):245-50. Epub 1969 Apr. 1.

109. Pelayo J C, Chenoweth D E, Hugli T E, Wilson C B, Blantz R C. Effects of the anaphylatoxin, C5a, on renal and glomerular hemodynamics in the rat. Kidney international. 1986; 30(1):62-7. Epub 1986 Jul. 1.

110. Gervasoni J E, Jr., Conrad D H, Hugli T E, Schwartz L B, Ruddy S. Degradation of human anaphylatoxin C3a by rat peritoneal mast cells: a role for the secretory granule enzyme chymase and heparin proteoglycan. J Immunol. 1986; 136(1):285-92. Epub 1986 Jan. 1.

111. Hugli T E, Marceau F. Effects of the C5a anaphylatoxin and its relationship to cyclo-oxygenase metabolites in rabbit vascular strips. British journal of pharmacology. 1985; 84(3):725-33. Epub 1985 Mar. 1.

112. Heideman M, Hugli T E. Anaphylatoxin generation in multisystem organ failure. The Journal of trauma. 1984; 24(12):1038-43. Epub 1984 Dec. 1.

113. Morgan E L, Weigle W O, Hugli T E. Anaphylatoxin-mediated regulation of human and murine immune responses. Federation proceedings. 1984; 43(10):2543-7. Epub 1984 Jul. 1.

114. Morgan E L, Thoman M L, Weigle W O, Hugli T E. Anaphylatoxin-mediated regulation of the immune response. II. C5a-mediated enhancement of human humoral and T cell-mediated immune responses. J Immunol. 1983; 130(3):1257-61. Epub 1983 Mar. 1.

115. Weigle W O, Morgan E L, Goodman M G, Chenoweth D E, Hugli T E. Modulation of the immune response by anaphylatoxin in the microenvironment of the interacting cells. Federation proceedings. 1982; 41(14):3099-103. Epub 1982 Dec. 1.

116. Morgan E L, Weigle W O, Hugli T E. Anaphylatoxin-mediated regulation of the immune response. I. C3a-mediated suppression of human and murine humoral immune responses. The Journal of experimental medicine. 1982; 155(5):1412-26. Epub 1982 May 1.

117. Stimler N P, Bach M K, Bloor C M, Hugli T E. Release of leukotrienes from guinea pig lung stimulated by C5ades Arg anaphylatoxin. J Immunol. 1982; 128(5): 2247-52. Epub 1982 May 1.

118. Stimler N P, Brocklehurst W E, Bloor C M, Hugli T E. Anaphylatoxin-mediated contraction of guinea pig lung strips: a nonhistamine tissue response. J Immunol. 1981; 126(6):2258-61. Epub 1981 Jun. 1.

119. Gerard C, Hugli T E. Identification of classical anaphylatoxin as the des-Arg form of the C5a molecule: evidence of a modulator role for the oligosaccharide unit in human des-Arg74-05a. Proceedings of the National Academy of Sciences of the United States of America. 1981; 78(3):1833-7. Epub 1981 Mar. 1.

120. Stimler N P, Brocklehurst W E, Bloor C M, Hugli T E. Complement anaphylatoxin C5a stimulates release of SRS-A-like activity from guinea-pig lung fragments. The Journal of pharmacy and pharmacology. 1980; 32(11): 804. Epub 1980 Nov. 1.

121. Hugli T E, Erickson B W. Synthetic peptides with the biological activities and specificity of human C3a anaphylatoxin. Proceedings of the National Academy of Sciences of the United States of America. 1977; 74(5): 1826-30. Epub 1977 May 1.

122. Mahler F, Intaglietta M, Hugli T E, Johnson A R. Influence of C3a anaphylatoxin compared to other vasoactive agents on the microcirculation of the rabbit momentum. Microvascular research. 1975; 9(3):345-56. Epub 1975 May 1.

The invention claimed is:

1. A method for species-independent quantitative measurement of a level of C3 or C4 in non-human animals, comprising:
   a) mixing 3-100 microliters of a specimen comprising anticoagulated blood, plasma, or serum of a non-human animal with a specificity converting protein matrix (SCM) to form a specimen/SCM mixture, wherein the SCM is derived from a human serum and the non-human animal is selected from the group consisting of a bovine, a chicken, a goat, a guinea pig, a horse, a mouse, a pig, a rabbit, a rat, a sheep, a turkey, and a dog;
   b) mixing the specimen/SCM mixture and an activator of the C system (Act) to form a specimen/SCM/Act mixture, wherein the activator is zymosan or heat aggregated gamma globulin (HAGG);
   c) incubating the specimen/SCM/Act mixture at a temperature between 36° C. to 38° C. for a time of between about 5-120 minutes;
   d) measuring an amount of human SC5b-9 by a human-specific ELISA in the specimen/SCM/Act mixture, wherein the measuring the amount of human SC5b-9 is proportional to the level of the non-human animal C3 or C4 in the specimen;
   e) measuring known amounts of the non-human animal C3 or C4 by the human-specific SC5b-9 ELISA and generating a calibration formula; and
   f) quantifying the amount of non-human animal C3 or C4 in the specimen by correlating the measured amount of human SC5b-9 from step (d) to the calibration formula;
   wherein the measuring of human SC5B-9 is species-independent.

2. A method according to claim 1, wherein in step a) the mixing of the specimen and the specificity converting protein matrix (SCM) is done at a low specimen/SCM ratio of 1:9 to 4:6.

3. The method according to claim 1, wherein the SCM in step a) is either C3-depleted normal human serum (C3depl-NHS) or lyophilized C3depl-NHS (lyoC3depl-NHS) or C4-depleted normal human serum (C4depl-NHS) or lyophilized C4-depleted normal human serum (lyoC4depl-NHS).

4. The method according to claim 1, wherein the SCM in step a) is supplemented with purified or recombinant human C5.

5. The method according to claim 1, wherein the SCM in step a) is supplemented with purified or recombinant human C5, C6, C7 and C9.

6. The method according to claim 1, wherein the SCM in step a) is a mixture of purified or recombinant human C5, C6, C7 and C9.

7. The method according to claim 1, wherein in step b) the activator of the C system (Act) is zymosan in a concentration ranging from 0.1-10 mg/mL or HAGG in a concentration ranging from 0.1-20 mg/mL.

8. The method according to claim 1, wherein in step c) the incubating of the specimen/SCM/Act mixture is done at 37° C. for 45-60 min with shaking.

9. The method according to claim 1, wherein the Act is heat aggregated gamma globulin (HAGG).

10. The method according to claim 1, wherein in step d) determining the production of one or more human proteins measures human SC5b-9 using a human CH50 kit.

11. The method of claim 1, wherein the SCM added to the mixture contains C5-9 in excess such that the method quantitates only the levels of the non-human animal C3 or C4.

12. A method for species-independent quantitative measurement of C3 in animals, comprising:
   a) obtaining a specimen comprising anticoagulated blood, plasma or serum of a non-human animal in an amount ranging from 3-100 microliters, wherein the specimen is obtained from a bovine, chicken, goat, guinea pig, horse, mouse, pig, rabbit, rat, sheep, turkey or dog;
   b) mixing the specimen with a specificity converting protein matrix (SCM) to form a specimen/SCM mixture, wherein SCM is either C3-depleted normal human serum (C3depl-NHS) or lyophilized C3depl-NHS (lyoC3depl-NHS);
   c) mixing the specimen/SCM mixture and an activator of the C system (Act) to form a specimen/SCM/Act mixture, wherein the Act is zymosan or heat aggregated gamma globulin (HAGG);
   d) incubating the specimen/SCM/Act mixture at a temperature between 36° C. to 38° C. for a time of between about 5-120 minutes;
   e) measuring an amount of human SC5b-9 by a human SC5b-9 ELISA, wherein the measuring the amount of human SC5b-9 is proportional to the level of the non-human animal C3 in the specimen,
   f) measuring known amounts of the non-human animal C3 by the human-specific SC5b-9 ELISA and generating a calibration formula; and
   g) quantifying the amount of non-human animal C3 in the specimen by correlating the measured amount of human SC5b-9 from step (e) to the calibration formula;
   wherein the measuring of human SC5B-9 is species-independent.

13. The method according to claim 12, wherein the SCM is C3-depleted normal human serum (C3depl-NHS).

14. The method according to claim 12, wherein, in step a) the specimen is serum of a bovine.

15. The method of claim 12, wherein the SCM added to the mixture contains C5-9 in excess such that the method quantitates only the levels of the non-human animal C3 or C4.

* * * * *